(12) United States Patent
Emrich et al.

(10) Patent No.: US 6,221,584 B1
(45) Date of Patent: *Apr. 24, 2001

(54) METHOD OF DETECTING TELOMERASE ACTIVITY

(75) Inventors: Thomas Emrich, Iffeldorf; Hermann Leying, Bichl; Matthias Hinzpeter, München; Gerlinde Karl, Garmisch-Partenkirchen, all of (DE)

(73) Assignee: Roche Diagnostics GmbH, Manheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,857

(22) PCT Filed: Nov. 27, 1996

(86) PCT No.: PCT/EP96/05245

§ 371 Date: Dec. 29, 1997

§ 102(e) Date: Dec. 29, 1997

(87) PCT Pub. No.: WO97/20069

PCT Pub. Date: Jun. 5, 1997

(30) Foreign Application Priority Data

Nov. 28, 1995 (DE) .............................................. 195 44 317
Oct. 24, 1996 (DE) .............................................. 196 44 302

(51) Int. Cl.[7] .............................. C12Q 1/68; C12P 19/34; C07H 21/04
(52) U.S. Cl. .......................... 435/6; 435/91.2; 435/91.21; 435/91.5; 435/183; 435/174; 435/194; 536/24.32; 536/24.33
(58) Field of Search ........................... 435/6, 91.2, 91.21, 435/91.5, 183, 194, 174; 536/24.31, 24.32, 24.33

(56) References Cited

U.S. PATENT DOCUMENTS

| | | | |
|---|---|---|---|
| 5,231,015 | * | 7/1993 | Cummins et al. ...................... 435/29 |
| 5,612,458 | * | 3/1997 | Hyldig-Nielsen et al. ..... 530/388.21 |
| 5,654,151 | * | 8/1997 | Allen et al. .............................. 435/6 |
| 5,837,453 | * | 11/1998 | Harley et al. ............................ 435/6 |
| 5,863,726 | * | 1/1999 | Harley et al. ............................ 435/6 |

FOREIGN PATENT DOCUMENTS 0 437 774A1   12/1990   (EP) .

OTHER PUBLICATIONS

Kim et al., Science, vol. 266, Dec. 23, 1994, "Specific Association of Human Telomerase Activity with Immortal Cells and Cancer".

International Publication No. WO95/13381, published May 18, 1995.

(List continued on next page.)

Primary Examiner—Carla J. Myers
(74) Attorney, Agent, or Firm—Arent Fox Kintner Plotkin Kahn

(57) ABSTRACT

The invention concerns a method for the detection of telomerase activity wherein (a) a sample to be tested is provided, (b) a first primer suitable as a telomerase substrate and nucleoside triphosphates are added and the reaction mixture is incubated under conditions under which a primer extension by the telomerase can take place, (c) an amplification of the extension product produced by the telomerase is carried out, (d) the amplification product produced in step (c) is immobilized on a solid phase and (e) the immobilized amplification product is detected qualitatively or/and quantitatively. Furthermore the invention concerns a suitable reagent kit for carrying out the method.

48 Claims, 6 Drawing Sheets

OTHER PUBLICATIONS

International Publication No. WO 91/04753, published Apr. 18, 1991.

International Publication No. WO 93/09813 published May 27, 1993.

Wright et al., 1995, vol. 23, No. 18, Nucleic Acids Research, "Modifications of a telomeric repeat amplification protocol (TRAP) result in increased reliability, linearity and sensitivity".

International Publication No. WO 93/11261, published Jun. 10, 1993.

Counter et al., Proc. Natl. Acad. Sci. USA, vol. 91, pp 29–2904, Apr. 1994, "Telomerase acitivity in human ovarian carcinoma".

Morin, Cell, vol. 59, pp 521–529, Nov. 3, 1989, The Human Telomere Terminal Transferase Enazyme is a Ribonucleoprotein that Synthesizes TTAGGG Repeats.

Vink et al. Journal of Virology. 64:5626–5627, Nov. 1990.*

Landgraf et al. Analytical Biochemistry. 198:86–91, 1991.*

* cited by examiner

Fig.5
(SEQ ID No: 16)

```
      P1
     ─────  4779                        ←── FROM pSV2CAT ──→
AATCCGTCGA GCAGAGTTCC CGCCTGATGA ATGCTCATCC GGAATTCCGT ATGGCAATGA AAGACGGTGA GCTGGTGATA TGGGATAGTG TTCACCCTTG
                     ──────────────────────────            ──────────────────────────────────────────────────
                              TE-1-ST                                          TE-CAT
                                                                    4620
TTACACCGTT TCCATGAGCA AAACTGAAAC GTTTTCATCG CTCTGGAGTG AATACCACGA CGATTTCCGG CAGTTTCTGG TTAGGGTTAG GGTTAGCCGC GC
                                                                  ────────────────────────────  ─────────────
                                                                           TE-ACT-ST                 TE-ACT
```

METHOD OF DETECTING TELOMERASE ACTIVITY

The present invention concerns a method for the detection of telomerase activity as well as reagents suitable therefor.

Telomeres are specific structures at the ends of chromosomes and in the case of eukaryotic organisms they are composed of an accumulation of repeated defined nucleotide sequences (repeats) which for example contain the sequence TTAGGG in humans. In somatic cells each replication of the cell inevitably leads to a shortening of the telomere ends and once the telomere falls below a certain length this finally leads to cell death.

In contrast virus-transformed or immortalized cells do not exhibit a reduction in their telomere length. This is due to the activity of an endogenous ribo-nucleoprotein in these cells which is denoted telomerase and can counteract the telomere shortening in a reaction similar to reverse transcriptase.

Since according to previous findings the expression of telomerase is confined to tumour cells, germ cells and immortalized cells, this protein is a very promising parameter for the diagnosis of tumours and is also a target for tumour therapy (cf. e.g. the review articles by Greider, 1994, Curr. Oppin. Gen. Dev. 4, 203–211; Counter et al., 1994, Proc. Natl. Acad. Sci. USA 91, 2900–2904 and Hiyama et al., 1995, Nature Med. 1, 249–255).

The methods described in the literature for detecting telomerase activity are all based on an in vitro detection of the enzyme activity. At present it is not possible to immunologically detect the human enzyme since its protein sequence is not yet known. Only the sequence of the telomerase from tetrahymena was recently described (Collins et al., 1995, Cell 81, 677–686).

In the detection methods described in the literature one differentiates between two principle methods. The first method is based on a synthetic oligonucleotide derived from the telomere sequence which serves as a primer. This primer is added together with unlabelled dideoxynucleotides and a radioactively labelled deoxynucleotide to a sample e.g. a cell extract containing telomerase whereby the primer is specifically elongated by the telomerase and the product of synthesis is radioactively labelled in this process. The reaction mixture is subsequently separated by gel electrophoresis and the pattern of bands is visualized by exposure of an X-ray film with subsequent development (Morin, 1989, Cell 59, 521–529; Nilsson et al., 1993, Oncogene 9, 3043–3048).

A telomerase-specific elongation product is also firstly produced in the other detection method. However, this is amplified in a subsequent polymerase chain reaction (PCR) and simultaneously labelled by the addition of radioactive deoxynucleotides. The labelled PCR products are detected by gel electrophoresis (Kim et al., 1994, Science 266, 2011–2015).

WO 95/13381 describes a method for the detection of telomerase activity in which a cell extract to be tested is contacted with a primer which contains no telomere repeat sequences wherein the telomerase can catalyse an extension of the primer by attaching telomere repeat sequences. Subsequently an amplification step is carried out with addition of a second primer. The telomerase activity is finally detected by gel electrophoretic separation of the resulting amplification products.

However, these detection methods of the state of the art have some disadvantages. Thus the sensitivity of a detection method without an amplification step is too low for routine applications since quantities of extracts containing $10^6$ to $10^7$ cells have to be used. Therefore this method cannot be used to examine primary tumour material which is only available in a small amount. In addition the exposure time of the gels is in the range of two to seven days which is also due to the low sensitivity. The detection method comprising an amplification step does not have this disadvantage since only $10^5$ cell equivalents per test have to be used routinely and $10^3$ cell equivalents can be reproducibly detected. However, the exposure times for the gels are also still at least one day for this method (Kim et al., 1994, Supra; Chadeneau et al., 1995, Cancer Res. 55, 2533–2536).

Both of the detection methods described in the literature have the disadvantage that the labelling of the elongation product or of the PCR product has to be achieved with radioactive labelling groups in order to obtain satisfactory results. This leads to long exposure times and to the undesired formation of radioactive waste. Furthermore, the gel electrophoretic separation of the reaction mixture followed by subsequent exposure and development of an X-ray film is very labour intensive.

Moreover neither of the said methods allows a high sample throughput. They are not suitable for automation as is necessary for example for routine analysis or for an effector screening.

Thus the object of the present invention was to at least partially eliminate the disadvantages of the methods of the state of the art. This object is achieved by a method for the detection of telomerase activity characterized in that (a) a sample to be tested is provided, (b) a first primer suitable as a telomerase substrate and nucleoside triphosphates are added and the reaction mixture is incubated under conditions under which a primer extension by the telomerase can take place, (c) an amplification of the extension product produced by the telomerase is carried out, (d) the amplification product produced in step (c) is immobilized on a solid phase and (e) the immobilized amplification product is detected qualitatively or/and quantitatively.

surprisingly it was found that the specificity of the telomerase reaction is retained by immobilizing the amplification product i.e. a positive signal can be reproducibly attributed to a telomerase activity. Hence the gel electrophoretic separation of the reaction mixture required by the state of the art is superfluous. In addition a very high sensitivity is achieved. In certain test formats it is even possible to achieve a gain in sensitivity by the method according to the invention compared to the methods of the state of the art. In addition the use of non-radioactive labels is possible and preferred in the method according to the invention which avoids the difficulties which occur when handling radioactive substances. These advantages make the method according to the invention very well suited to routine applications in automated detection instruments.

The method according to the invention enables a specific detection of amplified telomerase extension products without requiring a separation of the reaction products. This could not have been simply expected since all amplification mixtures also contain unspecific byproducts such as e.g. primer dimers, repeat sequences in addition to the telomerase extension products. Thus one has to expect that these unspecific products would also be detected in the test using a capture or detection probe directed towards the repeat sequence. In addition it was to be expected that when an internal standard was added this would always be co-detected. However, surprisingly it was found that by selecting suitable hybridization conditions and optionally by the addition of unlabelled oligonucleotides which are complementary to the primer sequences a highly specific detection of telomerase extension products without a separation step is achieved.

The telomerase activity is preferably detected by using labelling groups in particular non-radioactive labelling groups. All known labelling groups can be used as non-radioactive labelling groups e.g. immunologically reactive groups, e.g. nucleotide analogues or haptens which can react with a detection antibody, enzymes such as peroxidase, galactosidase or alkaline phosphatase, fluorescent or luminescent groups e.g. electrochemi-luminescent groups or other detection groups such as NMR-active labelling groups or electron-dense groups.

Immunologically reactive groups are preferred such as nucleotide analogues e.g. halogen-derivatized nucleotides such as Br-dUTP or nucleotides derivatized with organic residues that contain at least one C atom such as $CH_3$-dCTP, or haptens e.g. digoxigenin, digoxin, fluorescein etc., luminescent groups such as luminescent metal complexes e.g. ruthenium complexes and fluorescent groups such as fluorescein.

On the one hand the non-radioactive labelling groups can be incorporated directly into the amplification product. This incorporation can for example be achieved by using labelled nucleotides or/and labelled primers. On the other hand the amplification products can also be indirectly labelled e.g. by using a suitable labelling probe i.e. a probe which itself contains one or several labelling groups and specifically hybridizes with the amplification product. Oligonucleotides or/and nucleic acid analogues can for example be used as labelling probes. The probe can be hybridized to the amplification product before or/and after the immobilization step.

Step (a) of the method according to the invention comprises the provision of a sample to be tested. This sample is preferably a cell extract, in particular an extract from human cells. However, the cell extract can also be derived from other eukaryotic organisms such as yeasts or tetrahymena. The cell extract is preferably produced by lysing cells in a buffer which contains 0.01–5% by weight of a non-ionic or/and zwitterionic detergent. On the other hand the sample can also be lysed by optionally repeated thawing/freezing. Subsequently insoluble components such as cellular residues are preferably removed by centrifugation or/and filtration and the supernatant is collected. Good results are obtained with a quantity of extract which corresponds to $10^2$ to $10^5$ cell equivalents. Even if only 1–10 cell equivalents are used, specific signals are still obtained. If the sample to be tested is tissue e.g. tumour tissue, 10–1000 ng tissue is preferably used for a test.

Step (b) of the method according to the invention comprises the addition of a single-stranded primer suitable as a telomerase substrate to the sample and the incubation of the resulting reaction mixture under conditions under which a primer extension by the telomerase can take place. The primer is preferably an oligodeoxyribonucleotide. The length of the primer is preferably 10–50 and particularly preferably 12–30 nucleotides. In this method one can on the one hand use a first primer which is free of telomere repeat sequences. A preferred example of such a primer is a primer P1 described by Morin et al., (1991), Nature 353, 454–456 with the nucleotide sequence shown in SEQ ID NO.1. In addition it was surprisingly found that primers are also suitable which are derived from the 5' region of a retroviral LTR sequence e.g. from the 5' region of the LTR sequence of HIV. An example of such a primer is shown in SEQ ID NO.2. Apart from single-stranded primers, double-stranded primers with a 3' overhang can also be used.

On the other hand one can also use a first primer which contains telomere repeat sequences e.g. the primer P1-Telo with the nucleotide sequence shown in SEQ ID NO.3.

If non-radioactive labelling groups are used, the extension step (b) is preferably carried out so that only unlabelled nucleoside triphosphates can be attached to the first primer. The reason for this is that when non-radioactively labelled nucleoside triphosphates are present in the reaction mixture which can be used as a substrate by the telomerase, a partial inhibition of the telomerase activity is found which leads to a somewhat less efficient primer elongation. Nevertheless in certain embodiments of the invention it is also possible to incorporate non-radioactive labelling groups during the primer extension.

However, non-radioactive labelling groups are preferably not introduced into the product until the subsequent amplification step (c). This can for example be achieved by using non-radioactively labelled CTP (not a component of the telomere repeat sequences). In this case the reaction can be carried out as a "one-pot reaction" without compartmentation. On the other hand the non-radioactively labelled nucleoside triphosphates can be contacted with the reaction mixture at a later time. This can for example be achieved by compartmentation in which the non-radioactively labelled nucleoside triphosphates are separated during the extension step (b) from the reaction mixture by a removable barrier e.g. a wax layer that is meltable at higher temperatures. On the other hand it is of course also possible to add the reactants sequentially.

In addition it can be preferable to carry out an additional template-independent elongation of the extension product produced by the telomerase after the extension step (b). This elongation is preferably achieved by means of an enzymatic reaction e.g. by attaching nucleotides e.g. by a polyadenylation using terminal transferase or by ligation of short DNA fragments by means of DNA ligase.

Step (c) of the method according to the invention comprises an amplification of the extension product produced by the telomerase. The type of amplification step is not critical for the method according to the invention. The amplification is typically achieved by adding a suitable enzyme that can polymerize nucleic acids e.g. a nucleic acid polymerase or a nucleic acid ligase. It is preferable to use a thermostable enzyme and to carry out the amplification in several cycles.

Two primers are preferably used for the amplification whereby the telomerase substrate can be used as a first primer and a suitable complementary primer can be used as the second primer. The amplification product is formed by enzymatic catalysis e.g. by a template-dependent DNA polymerase by attaching nucleotides to the first and second primer. The second primer can preferably hybridize with the telomere repeat sequence such as the primer P2 shown in SEQ ID NO.4. A so-called anchor primer is preferably used for this which contains a region which is not complementary to the telomere repeat sequence at its 5' end. Such an anchor primer has the advantages that no amplification products can be formed which are longer than the original template and that primer dimers which must also contain repeat sequences when using a primer containing repeat sequences are not elongated. Anchor primers are particularly preferably used which contain an extension free of repeat sequences at their 5' end which is at least 4 and in particular at least 5 nt long. The length of this sequence region is preferably 4–20 nucleotides. Anchor primers with a GC-rich sequence at their 5' end are most preferred. Oligonucleotides or nucleic acid analogues preferably with a length of 10–50 nt which have a sequence complementary to a telomere repeat sequence and at the 5' side thereof an extension free of the repeat sequence are generally suitable as a primer in a method for the detection of telomerase activity. An example of a suitable anchor primer with a 6 nt long anchor sequence on the 5' side is the primer TE-ACT shown in SEQ ID NO.5. A particularly preferred anchor primer is the primer TE-3.2 shown in SEQ ID NO.13. Particularly good test results are obtained with this primer and with analogous primers in which up to 3 nucleotides are missing at their 3' end compared to TE-3.2.

The enzyme is preferably a thermostable DNA polymerase which can be used to carry out the many amplification cycles without inactivation of the polymerase. A particularly preferred amplification method is the polymerase chain reaction method (PCR).

If an additional elongation e.g. by a terminal transferase is carried out after the extension, a second primer can be used for the subsequent amplification step (c) which is complementary to the sequence section that is attached by elongation to the extension product. An example of this is the primer P3 shown in SEQ ID NO.6.

Alternatively the amplification can be achieved by other methods known to a person skilled in the art. Thus the reaction can also be catalysed by a template-dependent DNA ligase in which case the amplification product is formed by attaching an oligodeoxyribonucleotide to the primer by means of the DNA ligase. The DNA ligase is preferably a thermostable DNA ligase and such a method is particularly preferably carried out by means of the ligase chain reaction (LCR) technique.

Step (d) of the method according to the invention comprises the immobilization of the amplification product on a solid phase. The wall of a reaction vessel can for example serve as a solid phase. Alternatively particulate solid phases can also be used. The solid phase is preferably selected from microtitre plates, microreaction vessels, membranes, microchips, BIOCORE™ systems (a sensor chip having a derivatized dextran hydrogel layer approximately 100 nanometers thick) and optionally magnetic microbeads. The immobilization step saves a large amount of time and is less laborious compared to the methods of the state of the art. In addition it enables a high sample throughput and automation e.g. for routine analysis or for screening for effectors.

In principle the amplification products can be immobilized on the solid phase using any known method e.g. by adsorptive binding. However, the immobilization is preferably achieved by specific interactions e.g. via anchor groups. Examples of suitable anchor groups are immunologically reactive groups which can react with a solid phase bound antibody or other groups which are capable of a high affinity binding to an immobilized partner. A preferred example of an anchor group is biotin which can bind with high affinity to a solid phase coated with avidin or streptavidin. The immobilization method described by Savoysky et al. (Nucleic Acids Res. 24 (1996), 1175–1176) can for example be used for high sample numbers in which a biotinylated telomerase extension primer is used so that products formed in the amplification reaction which contain biotin as an immobilization group. [Me-$^3$H]TTP is incorporated simultaneously during the amplification.

The biotinylated and [$^3$H]-labelled amplification products are immobilized on streptavidin-coated fluoromicroparticles. This immobilization is detected by scintillation measurement on the basis of interactions of β-quanta released by [$^3$H] with the fluoromicro-particles.

The introduction of anchor groups into the amplification product can be achieved at various stages of the method according to the invention. Thus one can for example use one or several primers which already contain anchor groups e.g. biotin groups. On the other hand biotinylated nucleotides can also be introduced by elongating the primary extension product e.g. with terminal transferase or with DNA ligase or in the amplification step (c).

However, in a preferred embodiment of the present invention, it is not at all necessary that the amplification product itself contains an anchor group. An anchoring to the solid phase can for example also be achieved by adding a capture probe which carries one or several anchor groups and which can stably hybridize with the amplification product under the reaction conditions. Examples of suitable capture probes are oligonucleotides which contain telomere repeat sequences or sequences that are complementary thereto and one or several anchor groups e.g. biotin groups. Capture probes are particularly preferred which contain an anchor group at their 5' end. The oligonucleotide P4 shown in SEQ ID NO. 7 containing a 5' biotin group can for example be used as a capture probe.

On the other hand nucleic acid analogues can also be used as capture probes e.g. peptidic nucleic acids (Nielsen et al. (1991), Science 254, 1497–1500 and Dueholm et al. (1994), J. Org. Chem. 59, 5767–5773). Peptidic nucleic acids have a backbone linked by acid amide bonds which contains nucleobases as side groups. The use of peptidic nucleic acids as capture probes—and also as labelling probes—is preferred in particular embodiments of the method according to the invention.

Step (e) of the method according to the invention comprises the qualitative or/and quantitative detection of the amplification product. The detection is achieved in a well-known manner by means of the labelling groups contained in the amplification product or via the labelling probes bound to the amplification product. The detection is preferably carried out using non-radioactive labelling groups in automated measuring devices. Measuring devices are preferred in which the labelling groups are detected by calorimetric or/and spectrophotometric methods e.g. by enzymatic conversion of a substrate or by chemiluminescence or fluorescence.

The detection is preferably carried out under those conditions which enable a specific detection of amplified telomerase extension products even in the presence of unspecific byproducts. For this hybridization conditions can be selected which allow such a specific detection or/and unlabelled oligo-nucleotides or nucleic acid analogues (competitors) which are complementary to the primer sequences are added to the mixture so that these sequence regions are masked and the capture or detection probe can specifically hybridize with internal sequences of the amplification product.

Examples of suitable hybridization conditions are 37° C. and a formamide-free or formamide-containing buffer (e.g. 5×SSC, 10% formamide, 0.1% sarkosyl, 0.02% SDS, 1% blocking reagent in maleic acid buffer). Examples of suitable unlabelled competitors are the oligonucleotides shown in SEQ ID NO: 14 and 15.

Some preferred embodiments of the test procedure are stated in the following:

Version 1:

A primer which is free of telomere-specific repeats is used as a telomerase substrate e.g. one having the sequence shown in SEQ ID NO. 1 or 2. Alternatively a primer containing a repeat e.g. P1-Telo (SEQ ID NO. 3) can be used. This primer is used together with unlabelled nucleoside triphosphates dATP, dGTP and dTTP in the extension step (b). The extension product produced by the telomerase is then subjected to an amplification in step (c). The components required for the amplification can already be present in the reaction mixture in step (b) provided they do not interfere with the extension reaction. Other components are present in a compartmentalized form in the same reaction vessel e.g. under a meltable wax layer.

The reaction mixture in step (c) contains, in addition to the components already present in step (b), a second primer which contains a sequence complementary to the human telomere repeat sequence e.g. the primer P2 with the sequence shown in SEQ ID NO. 4 or the primer TE-ACT with the sequence shown in SEQ ID NO. 5, at least one nucleoside triphosphate provided with an anchor group e.g. biotinylated dUTP, at least one non-radioactively labelled nucleoside triphosphate e.g. Br-dUTP, Br-dCTP, $CH_3$-dCTP, DIG-dUTP or DIG-dCTP and a thermostable DNA polymerase e.g. Taq-polymerase.

The immobilization of the amplification product according to step (d) is carried out on a microtitre plate which is coated with a conjugate of streptavidin and bovine serum albumin. The amplification product is subsequently detected with the aid of a conjugate composed of an antibody or antibody fragment directed towards the labelling group e.g. Br-dU, Br-dC, $CH_3$-dC or DIG and an enzyme e.g. peroxidase.

Version 2:

Alternatively to version 1 the telomerase extension product produced in step (b) is elongated with the aid of terminal transferase and one or several nucleotides e.g. dATP. In this case the amplification is achieved by adding an oligo-dT primer e.g. the primer P3 with the sequence shown in SEQ ID NO. 6 as well as labelled and unlabelled nucleotides (see version 1). The amplification product is detected as described above.

This version offers advantages of sensitivity since it is possible to additionally introduce labelling groups (ca. 50–100 labelling groups per amplification product). This is of particular importance for short telomere products. In addition telomerase-catalysed full length extension products are exclusively amplified in this experimental procedure since a hybridization with repeat sequences within the elongation product is excluded by the selection of the primer. This also leads to an increased density of labelling groups.

Alternatively the amplification products can be immobilized in versions 1 and 2 by using a biotinylated first or/and second primer instead of incorporating biotinylated nucleoside triphosphate. The primers can for example be biotinylated at their 5' end.

Version 3:

In contrast to versions 1 and 2 an amplification product is produced which only contains labelling groups but no solid phase anchor groups. Therefore in this version only a single labelling of the DNA by adding non-radioactively labelled nucleotides is carried out during the PCR. The immobilization is achieved by denaturing the amplification products with subsequent hybridization to biotinylated capture probes e.g. an oligonucleotide with the nucleotide sequence shown in SEQ ID NO. 7.

In all variants a sequential test procedure without compartmentation by wax is alternatively possible. The maximum duration of all test procedures is ca. 10 h and preferably 6 to 8 h at most. A schematic representation of versions 1–3 of the method according to the invention is shown in FIG. 1.

Version 4:

The telomerase-catalysed extension of the telomerase substrate e.g. of the primer P1 or of a biotinylated primer P1 is carried out analogously to version 1. This is followed by an amplification of the extension product with addition of a second primer e.g. the primer TE-ACT. The amplification is carried out in the absence of labelled nucleotides. Hence no compartmentation is necessary during step (b). After the amplification the amplification products are denatured analogously to version 3 and hybridized with (i) a labelling probe e.g. an oligonucleotide containing DIG groups when using a biotinylated primer or (ii) with a labelling probe and a biotinylated capture probe when using non-biotinylated primers. The detection is carried out as described in version 1.

In addition the amplification reaction can be standardized by adding a pre-determined amount of an amplification standard in a preferred embodiment of the method according to the invention.

Such an amplification standard can for example be produced by inserting an arbitrary DNA sequence that is not contained in the telomerase extension products on the 3' side of the sequence corresponding to the first primer with the aid of recombinant techniques after cloning a telomerase extension product into a cloning vector. A defined amount of this construct is then added to the mixture during the amplification reaction and amplified together with the telomerase extension products with the aid of the first and second primer. An aliquot of the amplification mixture is then analysed with the aid of a first capture probe and a further aliquot is analysed with the aid of a second capture probe. The first capture probe enables amplification products to be detected which result from the telomerase elongation products as well as from the added standard whereas the second capture probe merely enables a detection of the amplification products derived from the standard. A standardization of the measured values based on the standard values then allows a quantitative statement of the telomerase activity in the tested sample.

If 2 or several different labelling groups are used which are selected such that they can be detected in parallel it is possible to carry out several detections sequentially in the same reaction vessel e.g. detection of the telomerase extension products and of the standard i.e. it is not necessary to examine two separate aliquots.

A further advantage of the method according to the invention is that standards can be used which, when detecting the telomerase extension products e.g. by immunoblot after gel electrophoresis, result in a band which is located outside the bands of the telomerase extension products. This enables an improved quantification.

Alternatively, if the capture probes are selected accordingly, it is possible to only immobilize the amplification products resulting from the standard using the first capture probe and only to immobilize the amplification products derived from the telomerase extension product using a second capture probe.

Examples of suitable amplification standards are shown in SEQ ID NO. 8 and FIG. 5. An example of a capture probe which is specifically suitable for detection of the amplification standard shown in SEQ ID NO. 8 is the oligonucleotide P5 shown in SEQ ID NO. 9. The detection of the standard shown in FIG. 5 can for example be carried out using the oligonucleotide TE-CAT shown in SEQ ID NO. 9.

Yet a further subject matter of the present invention is a reagent kit for the detection of telomerase activity comprising (a) a primer suitable as a telomerase substrate,
(b) nucleoside triphosphates,
(c) agents for the amplification of the telomerase extension product,
(d) labelling groups
(e) solid phase anchor groups and
(f) a solid phase.

The labelling groups are preferably non-radioactive labelling groups and can be present in the form of appropriately labelled nucleoside triphosphates or/and labelled primers. On the other hand the labelling groups can also be present on one or several labelling probes which hybridize under the test conditions with the amplification product.

The solid phase anchor groups are preferably biotin and the solid phase is coated with streptavidin or/and avidin. The solid phase is preferably selected from microtitre plates, microreaction vessels, membranes, microchips, biocore systems and optionally magnetic microbeads.

The solid phase anchor groups can on the one hand be present in the form of appropriately modified nucleoside triphosphates or on a primer. On the other hand the solid phase anchor groups can also be present on a capture probe which hybridizes with the amplification product.

The agents for amplifying the telomerase extension product preferably comprise a second primer and an enzyme suitable for amplifying nucleic acids preferably a thermostable DNA polymerase.

In a particularly preferred embodiment the reagent kit contains one or several labelling or/and capture probes which have labelling or/and solid phase anchor groups and hybridize with the amplification product. The labelling and capture probes are preferably selected from oligonucleotides and nucleic acid analogues, in particular peptidic nucleic acids.

If desired the reagent kit can also comprise agents for the further elongation of a telomerase extension product e.g. an enzyme such as terminal transferase or DNA ligase.

Moreover the reagent kit can also contain an internal standard for the quantification of the detection reaction and appropriate agents for the separate detection of the standard and amplification product.

Yet a further subject matter of the present invention is the use of an oligonucleotide from the 5' region of the LTR sequence of retroviruses as a telomerase substrate. The oligonucleotide is preferably derived from the 5' region of the LTR sequence of HIV and the oligonucleotide particularly preferably has a length of 10–50 nucleotides and comprises at its 3' end (a) the sequence shown in SEQ ID NO. 2, (b) a sequence which is at least 80% and in particular at least 90% homologous or (c) at least the 10 last nucleotides of a sequence according to (a) or (b).

The present invention is additionally elucidated by the following examples, sequence protocols and figures.

SEQ ID NO. 1 shows a primer (P1) suitable as a telomerase substrate;

SEQ ID NO. 2 shows a further primer (P-LTR) suitable as a telomerase substrate;

SEQ ID NO. 3 shows a further primer (P1-Telo) suitable as a telomerase substrate;

SEQ ID NO. 4 shows an amplification primer (P2);

SEQ ID NO. 5 shows an anchor primer (TE-ACT) suitable for the amplification;

SEQ ID NO. 6 shows an oligo-dT-primer (P3) suitable for the amplification;

SEQ ID NO. 7 shows a capture probe (P4);

SEQ ID NO. 8 shows an amplification standard for a quantitative determination of the telomerase activity by PCR;

SEQ ID NO. 9 shows a capture probe (P5) used for a standardized PCR mixture;

SEQ ID NO. 10 shows a further capture probe (TE-CAT) for a standardized PCR mixture;

SEQ ID NO. 11 and 12 show two primers (P1-ST and TE-ACT-ST) used to produce an amplification standard;

SEQ ID NO. 13 shows an anchor primer (TE-3.2) suitable for the amplification;

SEQ ID NO. 14 and 15 show two competitor oligonucleotides.

BRIEF DESCRIPTION OF THE DRAWINGS

FIG. 5 shows an amplification standard;

EXAMPLES

Figure 1:
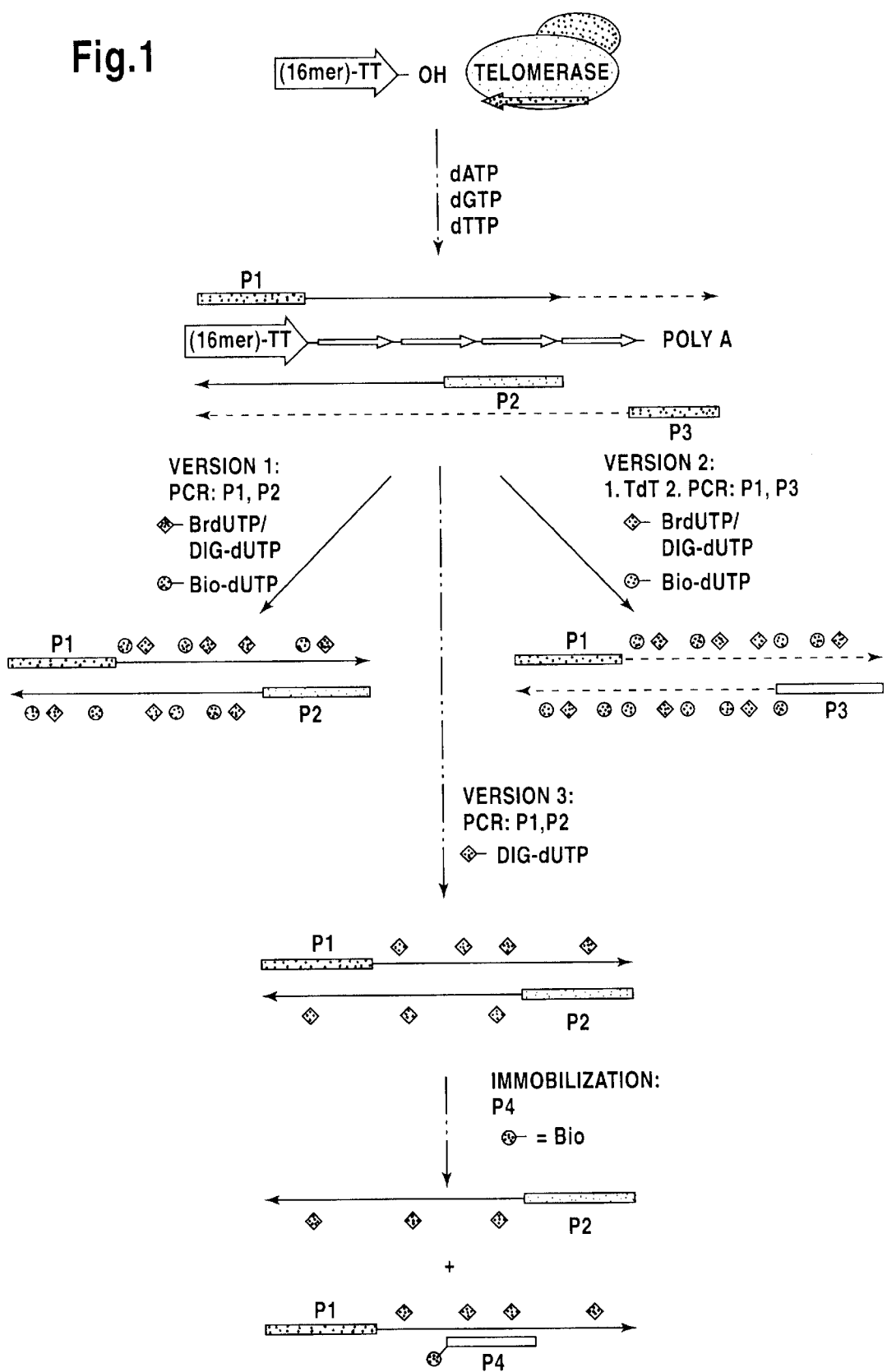
FIG. 1 shows a schematic representation of three preferred embodiments of the method according to the invention.

1. Reaction Mixture for the Detection of Telomerase According to Version 1 of the Method According to the Invention:

48 µl telomerase/PCR buffer (20 mM Tris-HCl, pH 8.3; 1.5 mM $MgCl_2$, 63 mM KCl, 0.05% Tween-20 (w/v); 1 mM EGTA, 40 µM dNTP (N=10 µM each of A, G, C, U), 300 nM primer P1 or P-LTR (SEQ ID NO. 1 or 2) or P1-Telo (SEQ ID NO. 3), 20 µg/ml T4g32 protein, 0.1 mg/ml bovine serum albumin (BSA) (w/v), 2 U Taq DNA polymerase) is placed in a precoated PCR reaction vessel. Then 2 µl of a sample (e.g. S 100 extract from $10^5$ cell equivalents) was added and incubated for 10–30 min at 25° C.

The precoated PCR reaction vessel contained the following components lyophilized at the bottom and over which a wax layer was poured (e.g AmliWax, Perkin Elmer): 100 ng primer P2 or TE-ACT (SEQ ID NO. 4 or 5; 223 nM in 50 µl), 30 ng DIG-dUTP (0.5 µM in 50 µl) and 370 ng biotinylated dUTP (7.5 µM in 50 µl).

Subsequently a PCR with 25 cycles (30 s at 94° C.; 30 s at 50° C., 90 s at 72° C.) was carried out. When heated to 94° C. the wax layer melted and the lyophilized reagents came into contact with the remaining reaction mixture.

After the PCR an aliquot of the mixture was transferred to a microtitre plate coated with streptavidin-thermo-BSA and incubated there for 30 min at 37° C. Afterwards it was washed three times with 200 µl washing buffer each time (150 mM NaCl, 15 mM Na-citrate, pH 7.0).

Then anti-DIG peroxidase conjugate was added (or another appropriate peroxidase conjugate when using another labelling group) and incubated for 60 minutes at 37° C. Then it was washed again three times with 200 µl washing buffer each time.

For the detection 200 µl TMB substrate reagent (100 µg/ml 3,3', 5,5'-tetramethylbenzidine, 1 mM citric acid, 100 mM Na acetate, 0.01% $H_2O_2$) was added. The detection was carried out in a multi-channel photometer at a wavelength of 450 nm.

2. Reaction Mixture for the Detection of Telomerase According to Version 2 of the Method According to the Invention:

The reaction was carried out as described under point 1 up to the telomerase extension step. Then 2.5 U/µl terminal transferase was added in 200 mM K cacodylate, 5 mM $CoCl_2$ and it was incubated for 60 min at 37° C.

Subsequently a PCR was carried out as described under point 1. The primer P3 with the sequence stated in SEQ ID NO. 6 was used instead of primer P2.

The amplification products were detected as described under point 1.

As an alternative to the methods described above the amplification products were also immobilized by using biotinylated telomerase/PCR primer (P1-Bio or P1. TeloBio) instead of incorporating biotinylated dUTP.

3. Reaction Mixture for the Detection of Telomerase According to Version 3 of the Method According to the Invention:

The telomerase extension was carried out as described under point 1. The precoated PCR reaction vessel contained the same components as described under point 1 but no biotinylated nucleoside triphosphate.

PCR was carried out as described under point 1. After the PCR 10 µl of the mixture was added to 40 µl denaturing buffer (125 mM NaOH, 0.2 mM EDTA) and incubated for 10 min at room temperature.

Then 450 µl hybridization buffer (62.5 mM Na phosphate, pH 6.5, 630 mM NaCl, 0.0625% BSA (w/v) and 1 µM biotinylated capture probe e.g. oligonucleotide P1-Bio or P4) was added and 200 µl of the mixture was transferred to a microtitre plate coated with SA-thermo BSA. Then it was incubated for 60 min at 37° C. and subsequently washed three times with 200 µl washing buffer each time.

The amplification products were detected as described under point 1.

All variants of the method according to the invention were also carried out alternatively using a sequential test procedure without compartmentation by wax. The total duration of all test formats was a maximum of 6 h.

4. Reaction Mixture for the Detection of Telomerase According to Version 4 of the Method According to the Invention:

The telomerase extension step was carried out as under point 1. Non-biotinylated as well as biotinylated primers were used as the telomerase substrate. In contrast to version 1 a precoated reaction vessel was not used.

The subsequent PCR was carried out as described under point 1 but in the absence of labelled nucleotides.

After the amplification a denaturation was carried out as described under point 3. When using a biotinylated primer a DIG-labelled labelling probe was used and when using a non-biotinylated primer a DIG-labelled labelling probe and a biotinylated capture probe were used.

The amplification products were detected as described under point 1.

5. Standardized Reaction Mixture:

A sequence region from the coding region of the bacterial enzyme chloramphenicol acetyl transferase was amplified with the aid of the primers P1-ST (SEQ ID NO. 11) and TE-ACT-ST (SEQ ID NO. 12). The resulting 202 Bp long PCR fragment (FIG. 5) contained sequences from the chloramphenicol acetyl transferase gene which are flanked by sequences of the two telomerase primers P1 (SEQ ID NO. 1) and TE-ACT (SEQ ID NO. 5).

In the telomerase extension step a defined amount of this PCR product (1–20 attomol) was added which—when using the appropriate primer—was amplified just as the telomerase extension products.

The detection and quantification of the standard was carried out by hybridizing a DIG-labelled CAT-specific primer TE-CAT (SEQ ID NO. 10) if biotinylated primer was added during the amplification or by hybridization with a biotinylated CAT-specific capture probe if the labelling groups were incorporated during the amplification.

6. Reaction Mixture PCR-ELISA

The telomerase extension step and the amplification were carried out in a single non-precoated reaction vessel.

For this the sample (1–3 µl cell extract corresponding to $1\times10^3$ to $3\times10^3$ cell equivalents or 1–50 µg total protein) or a positive control (extract from cells with a known telomerase activity) or a negative control (RNase-treated or heat-treated cell extract) was added to a reaction mixture which contained a biotinylated telomerase primer (e.g. P1, t-LTR or P1-Telo), an anchor primer (TE-ACT or TE-3.2), unlabelled dNTP and thermostable DNA polymerase.

The reaction mixture was placed in a thermocycler to carry out a combined primer elongation/amplification. Here a primer elongation was firstly carried out for 10–30 min at 25° C. Then it was heated for 5 min to 94° C. to inactivate the telomerase. Subsequently a PCR with 30 cycles was carried out as described under point 1 which was followed by a 10 minute heating to 72° C.

An aliquot of the amplification mixture was then denatured and hybridized with a DIG-labelled capture probe in the presence of unlabelled competitor oligonucleotides. The resulting product was immobilized by means of the biotin groups to a streptavidin coated microtitre plate.

The immobilized amplification products were detected as described under point 1. Alternatively the reaction mixture was separated by gel electrophoresis (e.g. non-denaturing polyacrylamide gel) and the bands were transferred to a membrane and visualized there.

7. Results:

The test formats described under points 1–3 are exemplified in FIG. 1.

Figure 2:
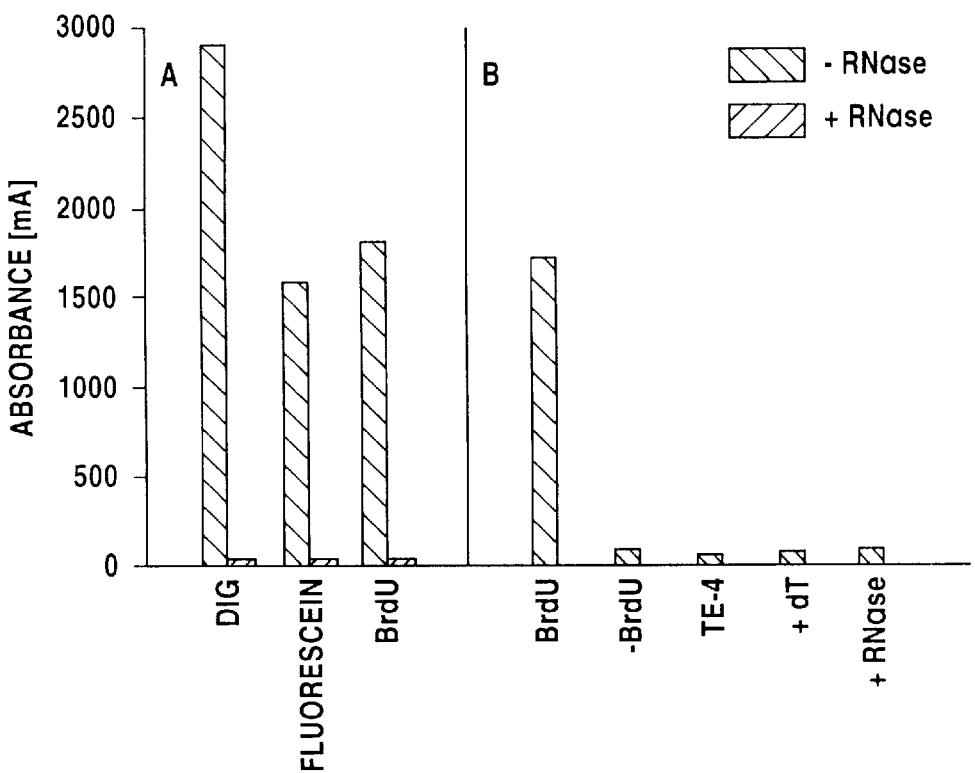
FIG. 2 shows the result of a non-radioactive detection of telomerase in a microtitre plate format.

FIG. 2 shows the non-radioactive detection of telomerase after immobilization on microtitre plates. $1\times10^5$ cell equivalents (HeLa extract) were used per 50 µl mixture (primer: P1-Bio). A: The labelling groups were introduced during the PCR step using the nucleotides stated in each case (DIG-dUTP, fluorescein-dUTP, Br-dUTP), the immobilization was carried out in a streptavidin-coated microtitre plate and the detection was carried out with the appropriate antibody conjugates. B: Specificity of the reaction: when RNase was added which inhibits the telomerase activity it was not possible to detect any amplification products.

Figure 3:
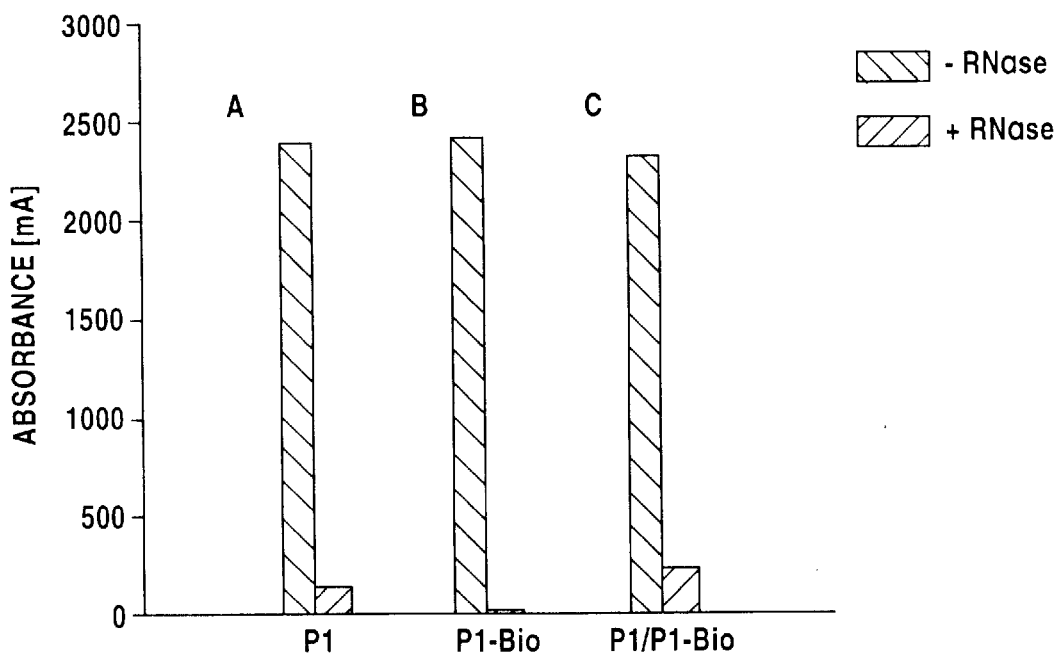
FIG. 3 shows a diagram of various test variants according to the invention.

FIG. 3 shows the result with various test formats. A: the result of a double labelling experiment (DIG-dUTP/Bio-dUTP) according to version 1; B: single labelling experiment (DIG-dUTP) using a biotinylated primer P1 (P1-Bio) according to version 1; C: single labelling experiment (DIG-dUTP) using the primer P1 as the telomerase substrate and the primer P1-Bio as the capture probe according to version 3.

Figure 4:
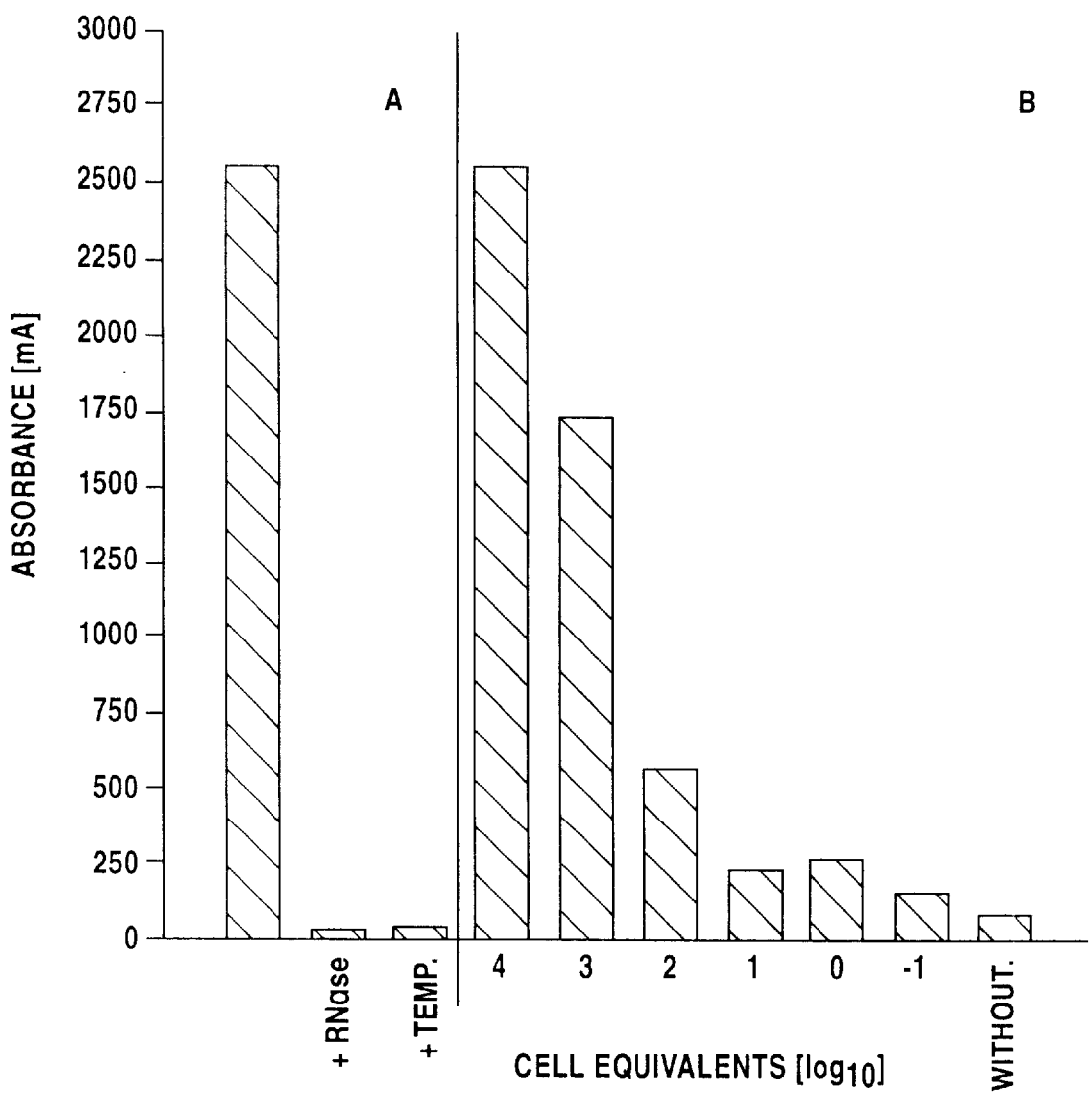
FIG. 4 shows the detection of telomerase in relation to the amount of extract used.

FIG. 4 shows the detection of telomerase in relation to the amount of extract used. A single labelling experiment (DIG-dUTP) according to version 1 was carried out using the biotinylated primer P1-Bio. A: Specificity of the test. The amplification product could no longer be detected after RNase or temperature treatment. B: Sensitivity of the test: starting with $1\times10^4$ cell equivalents the extract used (−/+

RNase treatment) was $\log_{10}$ titrated. 5% of the PCR mixture was subsequently used for the detection on a streptavidin-coated microtitre plate. It can be seen from FIG. 4 that 1–10 cell equivalents still result in signals which are clearly above the background (without).

Figure 6:
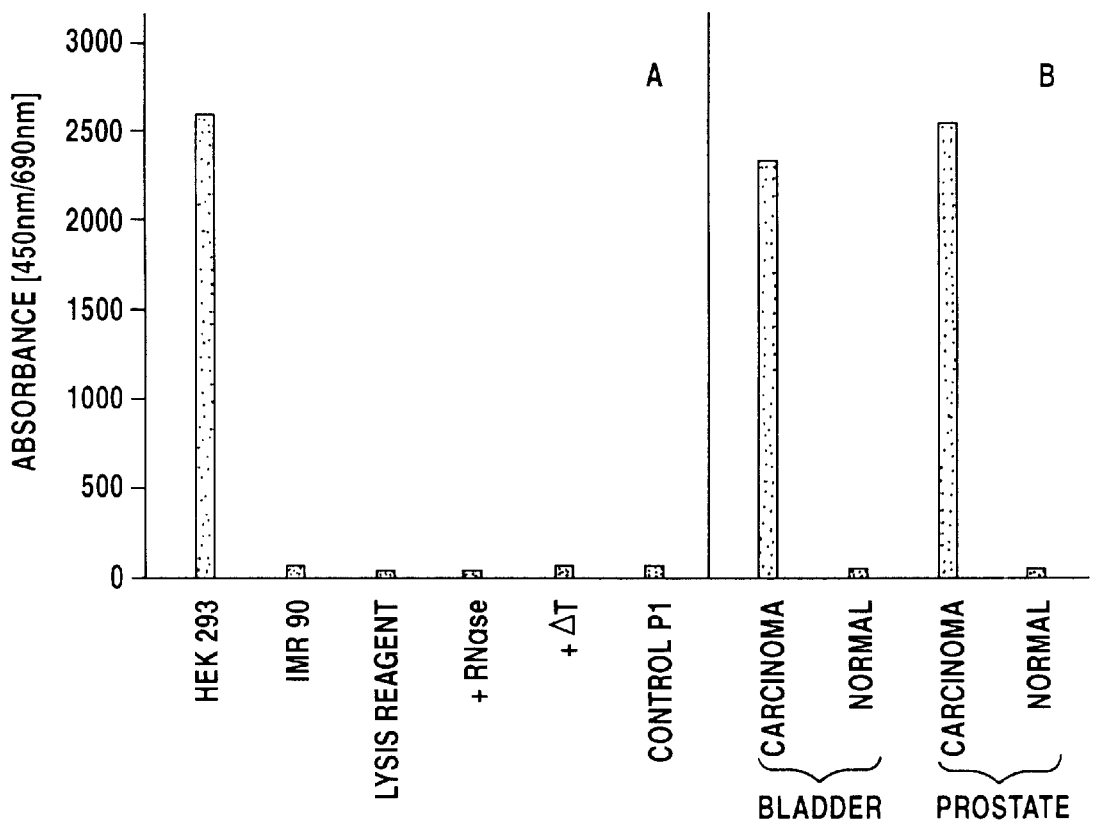
FIG. 6 shows the specificity of the detection of telomerase in cell lines and tissue samples and FIG. 7 shows the sensitivity of the telomerase detection in cell lines and tissue samples.

FIG. 6 shows the specific detection of telomerase activity in cell lines and tissue samples. A: The human telomerase-positive embryo kidney cell line 293 and human telomerase-negative lung fibroblast cell line EMR90 were analysed by a telomerase PCR-ELISA (point 6) according to the invention. A lysis reagent without extract (lysis reagent), 293 cells treated with RNase (+RNase) or heat-treated 293 cells (+ΔT) were used as negative controls. All controls gave negative results. The control P1 is a synthetic oligonucleotide which is not accepted by telomerase as a substrate. The tests were carried out as described under point 6 using an extract quantity corresponding to $1\times10^3$ cell equivalents in each case. B: The telomerase activity was analysed in normal tissue and primary tumour tissue obtained by biopsies. In this case a carcinoma of the prostate and a bladder carcinoma were each compared with normal prostate and bladder tissue (normal). The tests were carried out as described in section (A) using 20 μg total protein.

Figure 7:
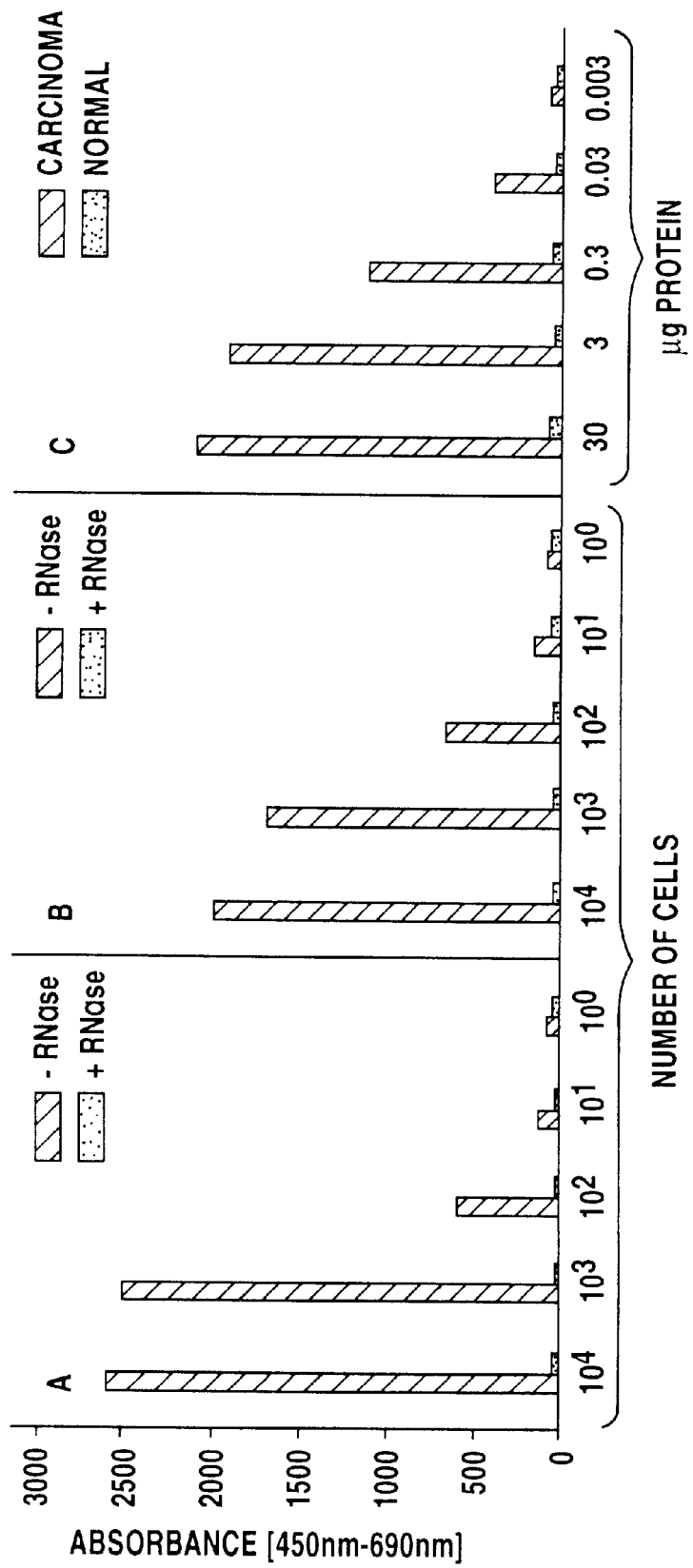

FIG. 7 shows the sensitivity of the telomerase PCR-ELISA according to the invention. A: An extract of telomerase-positive 293 cells was serially diluted with lysis reagent. The stated cell equivalents were analysed as described under point 6. The results are stated for RNase-treated extracts (+RNase) or extracts that were not treated with RNase (−RNase). B: 293-cells were serially diluted in culture medium before the lysis and then treated with lysis reagent as described above. The stated number of cells was analysed in the telomerase PCR-ELISA. The tests were carried out as described above. Results are stated for samples treated with RNase (+RNase) as well as for samples without RNase treatment (−RNase). C: The telomerase activity was measured in serially diluted extracts which were obtained from bladder carcinoma tumour tissue and normal bladder tissue. The stated amounts of tissue material were tested as described above.

What is claimed is:

1. A method for detecting a presence or an amount of telomerase activity, comprising:
combining, in a reaction vessel, (1) a sample suspected to contain telomerase, (2) a first primer which is suitable as a telomerase substrate and (3) a plurality of nucleoside triphosphates, to form a reaction mixture, and incubating the reaction mixture under conditions to extend the first primer in an extension reaction by adding nucleoside triphosphates to the first primer, wherein the extension reaction is mediated by the telomerase, to produce an extension product;
amplifying the extension product to produce amplification products;
immobilizing the amplification products on a solid phase; and
qualitatively or quantitatively detecting the amplification products immobilized in said immobilizing step, and correlating the detection with the presence or amount of telomerase activity, wherein the amplification products are detected via a labelling group which is provided on a detection probe which is hybridized with the amplification products in said detecting step.

2. The method of claim 1, wherein the amplification products are detected via a non-radioactive labelling group.

3. The method of claim 2, wherein the non-radioactive labelling group is selected from the group consisting of an immunologically reactive group, a luminescent group and a fluorescent group.

4. The method of claim 1, wherein said immobilizing step comprising adsorbing the amplification products on the solid phase.

5. The method of claim 1, wherein the amplification products are immobilized on the solid phase via an anchor group.

6. The method of claim 5, wherein the anchor group is biotin and the solid phase is coated with avidin and/or streptavidin.

7. The method of claim 1, wherein the solid phase is selected from the group consisting of a microtitre plate, a microreaction vessel, a membrane, a microchip and a microbead.

8. The method of claim 1, wherein said amplifying step is carried out using an enzyme.

9. The method of claim 8, wherein the enzyme is a thermostable enzyme.

10. The method of claim 8, wherein the enzyme is a nucleic acid polymerase or a nucleic acid ligase.

11. The method of claim 8, wherein said amplifying step is carried out using the first primer and a second primer.

12. The method of claim 8, wherein said amplifying step is achieved by PCR or LCR.

13. The method of claim 1, wherein the first primer is free of telomere repeat sequences.

14. The method of claim 13, wherein the first primer comprises a sequence from the 5' region of a retroviral LTR sequence.

15. The method of claim 14, wherein the retrovirus is HIV.

16. The method of claim 1, wherein the first primer contains telomere repeat sequences.

17. The method of claim 11, wherein the second primer contains a region at its 5' end which is not complementary to a telomere repeat sequence.

18. The method of claim 17, wherein the region has a length of at least 4 nucleotides.

19. The method of claim 18, wherein the region is a GC-rich region.

20. The method of claim 1, further comprising, between said combining step and said amplifying step, template-independently elongating the extension product to add an elongation sequence.

21. The method of claim 20, wherein said elongating step is carried out using an enzyme.

22. The method of claim 21, wherein the enzyme is terminal transferase.

23. The method of claim 20, wherein said amplifying step is carried out using the first primer and a second primer, and the second primer hybridizes with the elongation sequence.

24. The method of claim 1, wherein the nucleoside triphosphates which are added to the first primer are unlabelled.

25. The method of claim 1, wherein the amplification products are immobilized on the solid phase via an anchor group, wherein at least one of the following steps is conducted:
(a) providing the anchor group on the first primer;
(b) carrying out said amplifying step using the first primer and a second primer, and providing the anchor group on the second primer;
(c) incorporating a nucleoside triphosphate containing the anchor group into the amplification products produced in said amplifying step; and
(d) between said combining step and said amplifying step, template-independently elongating the extension product to add an elongation sequence, and providing the anchor group on the elongation sequence.

26. The method of claim 1, wherein said immobilizing step comprises hybridizing the amplification products with a capture probe containing an anchor group, and immobilizing the anchor group on the solid phase.

27. The method of claim 1, further comprising
before said amplifying step, combining a predetermined amount of an amplification standard with the reaction mixture;
amplifying the amplification standard along with the extension product in said amplifying step, to produce an amount of amplified standard; and quantitatively detecting the amount of the amplified standard and correlating the amount of the amplified standard with the amount of telomerase activity.

28. The method of claim 1, wherein the method is carried out in a single reaction vessel.

29. The method of claim 1, wherein said detecting step is carried out without separating the amplification products from any amplification artifacts produced in said amplifying step.

30. The method of claim 29, wherein said detecting step comprises combining with the reaction mixture unlabelled oligonucleotides or nucleic acid analogues which are complementary to the first primer.

31. The method of claim 11, wherein said detecting step is carried out without separating the amplification products from any amplification artifacts produced in said amplifying step, and said detecting step comprises combining with the reaction mixture unlabelled oligonucleotides or nucleic acid analogues which are complementary to the first primer or the second primer.

32. The method of claim 1, wherein the method is conducted using a reagent kit suitable for the detection of telomerase activity, comprising:
    the first primer;
    the plurality of nucleoside triphosphates;
    an agent which is suitable for amplifying the extension product to produce the amplification products;
    the detection probe;
    the labelling group which is provided on the detection probe;
    unlabelled oligonucleotides or nucleic acid analogues which are complementary to the first primer;
    a solid phase anchor group suitable for immobilizing the amplification products on the solid phase; and
    the solid phase.

33. The method of claim 32, wherein the labelling group is a non-radioactive labelling group.

34. The method of claim 32, wherein the solid phase anchor group is biotin and the solid phase is coated with streptavidin and/or avidin.

35. The method of claim 32, wherein the solid phase is selected from the group consisting of a microtitre plate, a microreaction vessel, a membrane, a microchip and a microbead.

36. The method of claim 32, wherein the solid phase anchor group is present on nucleoside triphosphates.

37. The method of claim 32, wherein the solid phase anchor group is present on the first primer.

38. The method of claim 32, wherein the reagent kit further comprises a capture probe having the solid phase anchor group thereon, and said immobilizing step comprises hybridizing the amplification products with the capture probe and immobilizing the anchor group on the solid phase.

39. The method of claim 32, wherein the detection probe is an oligonucleotide or a nucleic acid analogue.

40. The method of claim 38, wherein the capture probe is an oligonucleotide or a nucleic acid analogue.

41. The method of claim 39, wherein the detection probe is a peptidic nucleic acid.

42. The method of claim 40, wherein the capture probe is a peptidic nucleic acid.

43. The method of claim 32, wherein the reagent kit further comprises agents suitable for template-independently elongating the extension product to add an elongation sequence, and said method further comprises, between said combining step and said amplifying step, template-independently elongating the extension product to add the elongation sequence.

44. The method of claim 32, wherein the reagent kit further comprises an amplification standard, and said method further comprises, before said amplifying step, combining a predetermined amount of the amplification standard with the reaction mixture; amplifying the amplification standard along with the extension product in said amplifying step to produce an amount of amplified standard; and quantitatively detecting the amount of the amplified standard and correlating the amount of the amplified standard with the amount of telomerase activity.

45. The method of claim 1, wherein the first primer is an oligonucleotide having a length of 10–50 nucleotides which comprises at its 3' end at least 10 nucleotides of the sequence shown in SEQ ID NO: 2.

46. The method of claim 1, wherein said detecting step comprises hybridizing with the first primer unlabelled oligonucleotides or nucleic acid analogues which are complementary to the first primer so that the labelled detection probe can only hybridize with sequences of the amplification product made up of the nucleoside triphosphates which were added in the extension reaction.

47. The method of claim 11, wherein said detecting step comprises hybridizing with the first primer and the second primer unlabelled oligonucleotides or nucleic acid analogues which are complementary to each of the first primer and the second primer so that the labelled detection probe can only hybridize with sequences of the amplification product made up of the nucleoside triphosphates which were added in the extension reaction.

48. A method for detecting a presence or an amount of telomerase activity, comprising:
    combining, in a reaction vessel, (1) a sample suspected to contain telomerase, (2) a first primer which is suitable as a telomerase substrate and (3) a plurality of nucleoside triphosphates, to form a reaction mixture, and incubating the reaction mixture under conditions to extend the first primer in an extension reaction by adding nucleoside triphosphates to the first primer, wherein the extension reaction is mediated by the telomerase, to produce an extension product;
    amplifying the extension product to produce amplification products;
    immobilizing the amplification products on a solid phase; and
    qualitatively or quantitatively detecting the amplification products immobilized in said immobilizing step by hybridizing the amplification products with a detection probe and correlating the detection with the presence or amount of telomerase activity, wherein said detecting step further comprises hybridizing with the first primer unlabelled oligonucleotides or nucleic acid analogues which are complementary to the first primer so that the detection probe can only hybridize with sequences of the amplification product made up of the nucleoside triphosphates which were added in the extension reaction.

* * * * *

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1:

AATCCGTCGA GCAGAGTT                                      18

(2) INFORMATION FOR SEQ ID NO: 2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 2:

ACCCTTTTAG TCAGTGTGGA AAATCTCTAG CA                    32

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 3:

TTAGGGTTAG GGTTAGGG                                      18

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single

```
        (D) TOPOLOGY: linear (xi) SEQUENCE DESCRIPTION: SEQ ID NO: 4:

CCCTTACCCT TACCCTTACC CTAA                                              24

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 5:

GCGCGGCTAA CCCTAACCCT AACC                                              24

(2) INFORMATION FOR SEQ ID NO: 6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 6:

TTTTTTTTTT TTTTTTTMH                                                    19

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 7:

CCCTAACCCT AACCCTAACC CTAA                                              24

(2) INFORMATION FOR SEQ ID NO: 8:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO: 8:

GATCCAATCC GTCGAGCAGA GTTAACTACC TTCAACTCCA TCATGAGGGT TAGGGTTAGG        60

GATC                                                                    64

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 9:

CATGATGGAG TTGAAGGTAG TT                                                22

(2) INFORMATION FOR SEQ ID NO: 10:

(i) SEQUENCE CHARACTERISTICS:
        (A) LENGTH: 21 base pairs
        (B) TYPE: nucleic acid
```

(C) STRANDEDNESS: single
                (D) TOPOLOGY: linear (xi) SEQUENCE DESCRIPTION: SEQ ID NO: 10:

AAGACGGGTG AGCTGGTGAT A                                           21

(2) INFORMATION FOR SEQ ID NO: 11:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO: 11:

AATCCGTCGA GCAGAGTTCC CGCCTGATGA ATGCTC                           36

(2) INFORMATION FOR SEQ ID NO: 12:

(i) SEQUENCE CHARACTERISTICS:
                (A) LENGTH: 44 base pairs
                (B) TYPE: nucleic acid
                (C) STRANDEDNESS: single
                (D) TOPOLOGY: linear (xi) SEQUENCE DESCRIPTION: SEQ ID NO: 12:

GCGCGGCTAA CCCTAACCCT AACCAGAAAC TGCCGGAAAT CGTC                  44

(2) INFORMATION FOR SEQ ID NO: 13:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO: 13:

GGGCGGCCCT TACCCTTACC CTTACCCTAA                                  30

(2) INFORMATION FOR SEQ ID NO: 14:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO: 14:

CCTAACCCTA ACTCTGCT                                               18

(2) INFORMATION FOR SEQ ID NO: 15:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (xi) SEQUENCE DESCRIPTION: SEQ ID NO: 15:

GGGCGGCCCT TACCCTTA                                               18

(2) INFORMATION FOR SEQ ID NO: 16:

(i) SEQUENCE CHARACTERISTICS:
                (A) LENGTH: 202 base pairs
                (B) TYPE: nucleic acid
                (C) STRANDEDNESS: single -continued

```
        (D) TOPOLOGY: linear (xi) SEQUENCE DESCRIPTION: SEQ ID NO: 16:

AATCCGTCGA GCAGAGTTCC CGCCTGATGA ATGCTCATCC GGAATTCCGT ATGGCAATGA         60

AAGACGGTGA GCTGGTGATA TGGGATAGTG TTCACCCTTG TTACACCGTT TTCCATGAGC        120

AAACTGAAAC GTTTTCATCG CTCTGGAGTG AATACCACGA CGATTTCCGG CAGTTTCTGG        180

TTAGGGTTAG GGTTAGCCGC GC                                                 202
```